(12) United States Patent
Liu et al.

(10) Patent No.: US 7,837,757 B2
(45) Date of Patent: *Nov. 23, 2010

(54) ENHANCED ABSCISIC ACID AND FERTILIZER PERFORMANCE

(75) Inventors: Xiaozhong Liu, Vernon Hills, IL (US); Daniel F. Heiman, Libertyville, IL (US); Derek D. Woolard, Zion, IL (US); Yueh Wang, Arlington Heights, IL (US); Benjamin Belkind, Wilmette, IL (US); Prem Warrior, Green Oaks, IL (US); Gregory D. Venburg, Deerfield, IL (US); Peter D. Petracek, Grayslake, IL (US)

(73) Assignee: Valent BioSciences Corporation, Libertyville, IL (US)

(*) Notice: Subject to any disclaimer, the term of this patent is extended or adjusted under 35 U.S.C. 154(b) by 144 days.

This patent is subject to a terminal disclaimer.

(21) Appl. No.: 12/011,824

(22) Filed: Jan. 30, 2008

(65) Prior Publication Data

US 2008/0196464 A1 Aug. 21, 2008

Related U.S. Application Data

(60) Provisional application No. 60/898,591, filed on Jan. 31, 2007.

(51) Int. Cl.
*C05C 1/00* (2006.01)
*C05C 5/00* (2006.01)
*C05C 7/00* (2006.01)
*C05C 9/00* (2006.01)
*C05C 11/00* (2006.01)
*C05C 13/00* (2006.01)

(52) U.S. Cl. .................. 71/27; 71/28; 71/30; 71/31; 71/48; 71/49; 71/50; 71/53; 71/54; 71/58; 71/59; 71/60; 71/61; 71/63; 71/64.1

(58) Field of Classification Search ............... 71/11–63, 71/64.1

See application file for complete search history.

(56) References Cited

U.S. PATENT DOCUMENTS

| 4,581,057 A | 4/1986 | Nooden |
| 5,043,007 A * | 8/1991 | Davis .................. 504/100 |
| 7,405,181 B2 * | 7/2008 | Chang et al. ............. 504/117 |
| 2004/0035162 A1 * | 2/2004 | Williams et al. ............. 71/28 |
| 2004/0058818 A1 | 3/2004 | Li |
| 2006/0084573 A1 | 4/2006 | Grech et al. |

FOREIGN PATENT DOCUMENTS

CN 1213502 * 4/1999

* cited by examiner

*Primary Examiner*—Wayne Langel
(74) *Attorney, Agent, or Firm*—Wood, Phillips, Katz, Clark & Mortimer

(57) ABSTRACT

This invention relates to the use of nitrogen- or calcium-containing fertilizers to improve the performance of S-(+)-abscisic acid (S-ABA, ABA) or ABA salts on plants. This invention also relates to the use of ABA to reduce the phytotoxicity of foliar applied fertilizers.

18 Claims, No Drawings

ENHANCED ABSCISIC ACID AND FERTILIZER PERFORMANCE

FIELD OF THE INVENTION

The present invention relates to the use of adjuvants to improve the performance of abscisic acid (ABA) or salts thereof by increasing the extent and/or extending the duration of its desired biological activity. The present invention also relates to the use of ABA or its salts in conjunction with fertilizers such as nitrogen-containing fertilizers to reduce their phytotoxicity.

BACKGROUND OF THE INVENTION

Abscisic acid (ABA) is a natural occurring hormone found in all higher plants (Cutler and Krochko 1999, Trends in Plant Science, 4:472-478; Finkelstein and Rock 2002, The *Arabidopsis* Book, ASPB, Monona, Md., 1-52). ABA is involved in many major processes during plant growth and development including dormancy, germination, bud break, flowering, fruit set, general growth and development, stress tolerance, ripening, maturation, organ abscission and senescence. ABA also plays an important role in plant tolerance to environmental stresses, such as drought, cold and excessive salinity.

One key role of ABA in regulating physiological responses of plants is to act as a signal of reduced water availability to reduce water loss, inhibit growth and induce adaptive responses. All these functions are related to stomatal closure (Raschke and Hedrich 1985, Planta, 163: 105-118). When stomata close, plants conserve water to survive environmental stresses. However, stomatal closure also can result in reduced photosynthesis, respiration and growth. Stomatal closure is a rapid response of plants to ABA. The mechanism of this effect has been studied and has been shown to be due primarily to ABA effects on guard cell ion channels. Specifically, ABA blocks $H^+$ extrusion and $K^+$ influx from guard cells and promotes $K^+$, $Cl^-$, and malate extrusion and $Ca^{2+}$ influx. The net effect of ABA is to reduce the total osmotica in the guard cells, which in turn decreases the water content in the cell. This causes the guard cells to lose turgor and thus close the stomata (Assmann 2004, In: *Plant Hormones Biosynthesis, Signal Transduction, Action,* ed. Davies, p 391-412). The closing of the stomata results in reduced transpiration. The reduction of transpiration caused by stomatal closure is widely used as an experimental technique to indirectly identify and quantify ABA activity. The ability of ABA to reduce water use can not only extend the display shelf life of ornamentals or the postharvest shelf life of leafy plants, or promote drought tolerance, but it also can lead to a reduction in cold stress injury (Aroca et al. 2003, Plant Sci., 165: 671-679). ABA-induced reduction of stomatal conductance can lead to a decrease in photosynthesis (Downton et al. 1988 New Phytol., 108: 263-266) which in turn can lead to growth control. Improving the performance of ABA may be useful not only for improving the reduction of transpiration and water loss, but also for other uses of foliar applied ABA such as maintaining dormancy of buds and seeds, controlling fruit set, accelerating defoliation and enhancing color development of fruit such as grapes.

Surfactants or adjuvants have long been used with pesticides and plant growth regulators to increase the absorption or uptake by plants and thus improve the performance of the applied chemicals. Adjuvants include wetter-spreaders, stickers, penetrants, compatibility agents and fertilizers. However, there is little prior art information about adjuvant effects on ABA efficacy. In the patent application of Quaghebeur (2005, US20050198896 A1) it is noted that "ethoxylated sorbitan esters and siloxanes have proved to be particularly suitable for the application of ABA", but there is no mention of adjuvant effects on ABA efficacy. Lee et al. (1997, Kor. Soc. Hort. Sci. J., 38:717-721) reported that the addition of 0.05% Tween 20 (a commercially available ethoxylated sorbitan ester) improved ABA effect. However, Tween 20 is used for academic research and not packaged and distributed for the agricultural market.

The pH of an exogenously applied ABA solution may play a role in determining the efficiency of ABA uptake by plants. At an acidic pH, ABA is in its neutral undissociated form. This form is more lipophilic, and its penetration of the plant cuticle would be favored relative to the charged, dissociated form of ABA present at higher pHs (Blumenfeld and Bukovac 1972, Planta, 107:261-268). The uncharged undissociated form of ABA would more easily cross cell membranes from the relatively acidic apoplast into the cytosol.

Foliar applied nitrogen fertilizers, such as urea or ammonium nitrate, have been used in combination with plant growth regulators (PGRs) to improve the performance of the PGR. For example, the combination of the PGRs benzyladenine (Naito et al. 1974, J. Japan. Soc. Hort. Sci., 43: 215-223) or gibberellic acid (Shulman et al. 1987, Plant Growth Regul., 5: 229-234) with urea increased the grape berry sizing effect compared to the sizing effect achieved with the PGR alone. Ammonium salts have been reported to increase the absorption of pesticides (Wang and Liu 2007, Pestic. Biochem., Physiol., 87: 1-8). Nooden (1986, U.S. Pat. No. 4,581,057) claimed the use of ABA to increase fertilizer performance. However, there are no reports on the use of urea ($H_2NCONH_2$) or ammonium nitrate ($NH_4NO_3$) to improve ABA performance.

There are no reports on the use of calcium chloride ($CaCl_2$) or other calcium salts to improve ABA performance.

There are no reports on the use of magnesium nitrate ($Mg(NO_3)_2$) or other magnesium salts to improve ABA performance.

In order maximize the performance of ABA in its various agricultural and horticultural applications there is a need to improve the extent and duration of ABA efficacy.

Foliar application of nutrients has been used as an alternative approach to supplement nutrients to crops. Kuepper (2003, Appropriate Technology Transfer for Rural Areas. March 2003) reported that foliar fertilization increased crop yield and quality as well as resistance of crops to biotic and abiotic stress. The major advantage of foliar fertilization over ground fertilization is its efficiency of nutrient absorption in contrast, root absorption costs energy to transport nutrients from root to shoots. Also, foliar fertilization reduces nutrient loss and ground water contamination.

Foliar applications of nitrogen-fertilizer, however, do not always increase the yield of crops as expected. For example, foliar application of urea on soybean usually decreased the yield (Gray, 1977. Situation 77. Natl. Fertil. Dev. Ctr., Muscle Shoals, Ala. Bull. Y-115). The reduction of soybean yield was thought to be caused by leaf burn due to phytotoxicity of foliar urea fertilization (Krogmeier et al., 1989, Proc. Natl. Acad. Sci. USA. 86:8189-8191). Phytotoxicity of foliar fertilizer was affected by the form of nitrogen-fertilizer, concentration of fertilizer, and humidity or temperature of application to the site (Garcia and Hanway, 1976, Agron. J. 68, 653-657; Poole et al., 1983. Agronomy J. 75:201-203). Urea, the most popular nitrogen-fertilizer, was often observed to cause leaf burn after foliar fertilization. The application of granular fertilizer also has the potential to cause phytotoxicity leaf burn because leaves of turfgrass are close to the ground and readily contact granular fertilizer.

Foliar application of calcium supplements is also a typical management practice in many crops and in particular apple and other fruit trees. High doses of calcium also potentially cause phytotoxicity on the tree canopy. However, less attention has been paid to the reduction of calcium phytotoxicity.

Thus there is a need to reduce the phytotoxicity resulting from the foliar application of nitrogen containing fertilizers. A reduction in phytotoxicity would also enable the use of higher fertilizer rates and potentially less frequent applications.

Bremner (1995, Fertilizer Research 42:321-329) summarized approaches to reduce the phytotoxicity of urea, including (a) addition of an urease inhibitor to fertilizer; (b) coating of the fertilizer with sulfur or other materials to slow its rate of dissolution; (c) acidulation of the fertilizer with inorganic acids; (d) treatment of the fertilizer with inorganic salts; and (e) use of urea supergranules. Some of these approaches can also be used for other nitrogen-fertilizers.

ABA plays an important role in plant tolerance to environmental stresses, such as drought, cold, and excessive salinity. Nooden (1986, U.S. Pat. No. 4,581,057) claims the use of ABA to increase fertilizer activity. However, there are no reports on the use of ABA to reduce the phytotoxicity of fertilizers.

SUMMARY OF THE INVENTION

The present invention is directed toward the incorporation of an effective amount of a nitrogen and/or calcium containing fertilizer salt, or combination of such fertilizers or salts into an ABA-containing end-use solution composition or into a liquid or solid formulation composition intended for preparation of such an end-use solution in order to increase the effectiveness of ABA by increasing the extent and/or extending the duration of its desired biological activity. This is then accomplished by applying said end-use solution composition directly to target plants or the locus thereof by spraying or drenching.

The present invention is also directed to the incorporation of an effective amount of a nitrogen and/or calcium containing fertilizer or salt, or combination of such fertilizers or salts, into an ABA-containing end-use solution composition in order to decrease the ABA application rate required to attain a targeted degree or duration of ABA biological activity.

The present invention is also directed to the incorporation of an effective amount of nitrogen and/or calcium containing fertilizer or salt, or combination of such fertilizers or salts into an ABA-containing in bottle formulation in order to decrease the ABA application rate required to attain a targeted degree or duration of ABA biological activity.

The present invention relates to the addition of an effective amount of ABA or its salts to nitrogen and/or calcium containing fertilizers or salts to reduce their phytotoxicity during foliar application. This decrease in phytotoxicity would allow foliar fertilizer application rates to be increased.

The presently preferred nitrogen containing fertilizers are urea and/or ammonium nitrate.

The presently preferred calcium containing fertilizer or salt is calcium chloride.

DETAILED DESCRIPTION OF THE INVENTION

The compositions of the present invention improve ABA effectiveness by incorporating a nitrogen-containing fertilizer and optionally a calcium-containing supplement together with an effective amount of the plant growth regulator abscisic acid (S-ABA; ABA; S-(+)-abscisic acid; +-ABA, (+)-(S)-cis,trans-abscisic acid, (+)-(S)-cis,trans-ABA; S-ABA; (S)-5-(1-hydroxy-2,6,6,-trimethyl-4-oxo-2-cyclohexen-1-yl)-3-methyl-(2Z,4E)-pentadienoic acid; CAS registry no. [21293-29-8]). ABA effectiveness may be measured experimentally by quantifying the inhibition of transpiration in tomato leaves; this is a reliable laboratory bioassay of the level of ABA activity.

The compositions of the present invention comprise ABA or a salt thereof, together with a nitrogen and/or calcium containing fertilizer, or combination of such fertilizers, and applies to a ready-to-apply formulated liquid solution or to a mixture prepared by the end user of the ABA or to a solid or liquid formulation concentrate. The effectiveness of the compositions of the present invention was demonstrated by tomato leaf transpiration inhibition. The response of tomato plants to ABA is representative of the response of other plant species, such as nursery plants, to ABA. Other physiological processes regulated by ABA such as the promotion of drought tolerance of bedding plants, fruit coloration, dormancy of buds and seeds, plant growth control, defoliation, and chilling and freeze stress protection are expected to respond to the combinations of ABA or ABA salts with adjuvants of this invention.

Nitrogen-containing fertilizers for improving ABA performance include, but are not limited to, urea, nitrate salts such as ammonium nitrate, anhydrous ammonia, and other ammonium salts such as ammonium sulfate or ammonium acetate.

The presently preferred calcium-containing nutritional supplements or fertilizers for improving ABA performance are calcium chloride and calcium nitrate Optionally, a nitrogen containing fertilizer, such as urea or ammonium nitrate, can be utilized in combination with the calcium containing fertilizers in accordance with the present invention.

As used herein, the term "salt" refers to the water soluble salts of ABA or ABA analogs or derivatives, as appropriate. Representative such salts include inorganic salts such as the ammonium, lithium, sodium, potassium, calcium and magnesium salts and organic amine salts such as the triethanolamine, dimethylethanolamine and ethanolamine salts.

Depending on the target plant species, physiological processes of interest, and environmental conditions, the effective concentration of ABA can vary, but it is generally in the range of about 0.1 ppm to about 10,000 ppm, and preferably from about 1 to about 1000 ppm.

The preferred concentration of nitrogen and/or calcium containing fertilizer or salt in the end-use solutions of the present invention is generally in the range about 0.1 mM to about 1000 mM, preferably from about 1 to about 100 mM. Water is the carrier solvent in the end-use solutions.

Thus, a presently preferred composition of the present invention comprises from about 0.1 ppm to about 10,000 ppm ABA, from about 0.1 mM to about 1000 mM nitrogen and/or calcium containing fertilizer or salt and the balance consisting of water.

The effective concentration range of ABA depends on the water volume applied to plants as well as other factors such the plant age and size, the plant species and varietal sensitivity to ABA, and the targeted physiological process.

The invention is illustrated by, but is not limited by, the following representative examples.

EXAMPLES

Preparation of plant specimens for use in the treatment studies of the examples described was carried out as follows. Tomato (variety: Rutgers) seeds were sown in an 18-cell flat filled with Promix PGX (available from Premier Horticulture Inc. Quakertown, Pa.) and grown for 3 weeks to allow for germination and initial growth. Plants were then transplanted into pots (18 cm in diameter and 18 cm in height), filled with Promix BX (available from Premier Horticulture Inc. Quakertown, Pa.), and grown for one or two more weeks before treatment, depending on temperature and available light. Plants received daily irrigation and weekly fertilizer (1 g/L all purpose fertilizer 20-20-20, available from The Scotts Company, Marysville, Ohio).

All treatment solutions were prepared with distilled water. ABA (95% active ingredient) is available from Lomon Bio-Technology Co., Ltd. (Shichuan, China). Twenty L of 250 ppm ABA solution was prepared and stored in the dark at 20-25° C. This 250-ppm ABA solution was used for all studies to eliminate the possibility of applying an incorrect concentration of ABA.

Urea and ammonium nitrate ($NH_4NO_3$) are available from Sigma-Aldrich (St. Louis, Mo.).

Calcium chloride ($CaCl_2$) is available from Sigma-Aldrich (St. Louis, Mo.).

ABA solutions and blank treatments were applied to the aerial parts of tomato plant leaves at the rate of 20 mL per 6 plants. Plants were then placed in a transparent chamber with humidity controlled within the range of 40 to 60% relative humidity. Leaf transpiration rates were measured at 1, 2 and 3 days; at 1, 2, 3 and 4 days; or at 1, 2, 3, 4 and 7 days after treatment. Measurements were conducted using a LI-1600 Steady State Porometer (LI-Cor, Lincoln, Nebr.). Each day the transpiration rate of the plants of each treatment group was normalized to the percentage of the transpiration rate of untreated plants (plants sprayed with water only) in order to control for day-to-day variability caused by changes of environmental conditions such as light intensity and temperature. In some cases, data for each plant was averaged over a 3-day period to balance the short term and long-term effect of ABA on tomato leaf transpiration as well as to control for experimental variability.

All experiments were conducted using a randomized complete block experimental design. Data were analyzed by analysis of variance. Duncan's new multiple range tests at $\alpha=0.05$ were used for mean separations.

Example 1

The effect of foliar applied urea (1, 10 or 100 mM) alone or in combination with 250 ppm ABA on tomato leaf transpiration was examined (Table 1). Urea alone at 1, 10 or 100 mM did not reduce tomato leaf transpiration. However, plants treated with the combination of 10 or 100 mM of urea with 250 ppm ABA had significantly lower transpiration rates than plants treated with ABA alone. ABA with 100 mM urea reduced transpiration more than ABA with 10 mM urea. These results demonstrate that urea can be used as an adjuvant to improve ABA performance.

TABLE 1

Effect of foliar applied urea and its combination with ABA on tomato leaf transpiration inhibition.

| | Transpiration rate (% of control) Days after treatment | | | |
|---|---|---|---|---|
| Treatment | 1 | 2 | 3 | 4 |
| Control | 100 | 100 | 100 | 100 |
| 250 ppm ABA | 68 | 89 | 95 | 91 |
| 1 mM Urea | 103 | 98 | 98 | 100 |
| 10 mM Urea | 101 | 103 | 106 | 101 |
| 100 mM Urea | 102 | 102 | 107 | 102 |
| 250 ppm ABA + 1 mM Urea | 61 | 80 | 88 | 95 |
| 250 ppm ABA + 10 mM Urea | 42 | 60 | 78 | 90 |
| 250 ppm ABA + 100 mM Urea | 31 | 48 | 67 | 87 |

Example 2

The effect of foliar applied ammonium nitrate (1, 10 or 100 mM) alone or in combination with 250 ppm ABA on tomato leaf transpiration was examined (Table 2). Ammonium nitrate alone at 1, 10 or 100 mM did not reduce tomato leaf transpiration. However, plants treated with the combination of 10 or 100 mM of ammonium nitrate with 250 ppm ABA had significantly lower transpiration rates than plants treated with ABA alone. ABA with 100 mM ammonium nitrate reduced transpiration more than ABA with 10 mM ammonium nitrate. These results demonstrate that ammonium nitrate can be used as an adjuvant to improve ABA performance.

TABLE 2

Effect of foliar applied ammonium nitrate alone or in combination with ABA on tomato leaf transpiration inhibition.

| | Transpiration rate (% of control) Days after treatment | | | |
|---|---|---|---|---|
| Treatment | 1 | 2 | 3 | 4 |
| Control | 100 | 100 | 100 | 100 |
| 250 ppm ABA | 63 | 63 | 87 | 106 |
| 1 mM $NH_4NO_3$ | 107 | 107 | 106 | 83 |
| 10 mM $NH_4NO_3$ | 95 | 95 | 131 | 106 |
| 100 mM $NH_4NO_3$ | 97 | 97 | 128 | 107 |
| 250 ppm ABA + 1 mM NH4NO3 | 61 | 61 | 75 | 72 |
| 250 ppm ABA + 10 mM $NH_4NO_3$ | 35 | 35 | 75 | 73 |
| 250 ppm ABA + 100 mM $NH_4NO_3$ | 29 | 29 | 62 | 85 |

Example 3

Foliar applied urea (1, 10 or 100 mM) and ABA (250 ppm) combinations were compared to ammonium nitrate (1, 10 or 100 mM) and ABA combinations on their effect on tomato leaf transpiration (Table 3). At the same rate, the combination of urea and ABA inhibited transpiration more than the ammonium nitrate and ABA combination. These results demonstrate that urea is more effective than ammonium nitrate to improve ABA performance.

TABLE 3

Effect of foliar applied urea or ammonium nitrate on ABA performance as measured by inhibition of tomato leaf transpiration

| Treatment | Transpiration rate (% of control) |
|---|---|
| Control | 100 |
| 250 ppm ABA | 87 |
| 250 ppm ABA + 1 mM Urea | 79 |
| 250 ppm ABA + 10 mM Urea | 68 |
| 250 ppm ABA + 100 mM Urea | 48 |
| 250 ppm ABA + 1 mM $NH_4NO_3$ | 89 |
| 250 ppm ABA + 10 mM $NH_4NO_3$ | 86 |
| 250 ppm ABA + 100 mM $NH_4NO_3$ | 61 |

Data listed in this table are the average values over the first 3 days after treatment.

Example 4

Preparation of an Aqueous Solution Composition of the Ammonium Salt of (S)-(+)-Abscisic Acid Comprising Potassium Sorbate

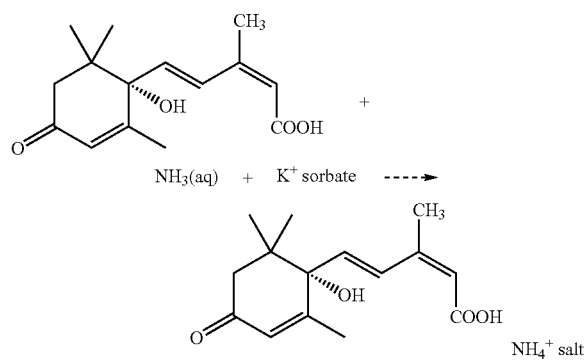

In a 600 mL beaker, 55 g of (S)-(+)-abscisic acid of 95% purity was added, followed by 500 μL of Tween 20 and 200 mL of water. Then, 10 mL of concentrated aqueous ammonia was added while stirring until the mixture came to equilibrium. Then, additional concentrated ammonia was added dropwise until all solid was dissolved. A homogenous solution was achieved when a total of about 13.5 mL of ammonia has been added. At this point, potassium sorbate (1.25 g) was added to the composition; it quickly dissolved. The mixture was transferred to a 500 ml volumetric flask and was brought up to 500 mL with deionized water. The mixture was stored in a brown glass bottle. The pH was measured to be 6.50.

An aqueous solution composition comprising 10% abscisic acid as the ammonium salt by weight and further comprising a naturally-occurring antimicrobial preservative was prepared.

Example 5

Preparation of an Aqueous Solution Composition of the Ammonium Salt of (S)-(+)-Abscisic Acid Comprising Ammonium Nitrate To a solution of 50 mg Tween 20 in 8 mL of water was added 2.64 g of (S)-(+)-abscisic acid (10 mmoles of 95% purity). Addition of the theoretical amount of concentrated aqueous ammonium and stirring briefly brought all the abscisic acid into solution. Ammonium nitrate (8.00 g, 100 mmoles) was added, and it dissolved within a few minutes. Potassium sorbate (63 mg) was added as an antimicrobial preservative, and it dissolved within a few minutes. The solution was made up to a final volume of 25 mL by addition of deionized water.

An aqueous solution composition comprising 10% abscisic acid by weight as the ammonium salt and further comprising 32% by weight ammonium nitrate as a performance enhancing additive was prepared.

Example 6

Preparation of an Aqueous Solution Composition of the Ammonium Salt of (S)-(+)-Abscisic Acid Comprising Both Ammonium Nitrate and Urea A solution of ammonium nitrate (8.00 g, 100 mmoles) and urea (6.01 g, 100 mmoles) was prepared in 7 mL of water. Tween 20 (50 mg) was added, followed by 2.64 g of (S)-(+)-abscisic acid (10 mmoles of 95% purity). The abscisic acid was dissolved by addition of the theoretical amount of concentrated aqueous ammonia plus 2 mL more deionized water. The solution was made up to 25 mL volume by addition of deionized water and filtered.

An aqueous solution composition comprising 10% abscisic acid by weight as the ammonium salt and further comprising 32% by weight ammonium nitrate plus 24% by weight of urea as performance enhancing additives was prepared.

Example 7

Preparation of an Aqueous Solution Composition of the Ammonium Salt of (S)-(+)-Abscisic Acid Comprising Both Ammonium Nitrate and Calcium Chloride A solution of calcium chloride dihydrate (14.7 g, 100 mmoles) was prepared in 10 mL of water. Tween 20 (50 mg) was added, followed by 2.64 g of (S)-(+)-abscisic acid (10 mmoles of 95% purity). Addition of the theoretical amount of concentrated aqueous ammonia produced a gummy mixture. Addition of ca. 30 mL additional deionized water and stirring overnight finally gave a clear solution. Ammonium nitrate (8.00 g, 100 mmoles) was added, and it dissolved easily. The volume of the final solution was measured to be 67 mL, corresponding to 3.7% (S)-(+)-abscisic acid by weight to volume.

An aqueous solution composition comprising 3.7% abscisic acid by weight as the ammonium salt and further comprising 11.9% by weight ammonium nitrate plus 21.9% calcium chloride dihydrate as performance enhancing additives was prepared.

Example 8

Preparation of an Aqueous Solution Composition of the Ammonium Salt of (S)-(+)-Abscisic Acid Comprising Magnesium Nitrate A solution was prepared by dissolving 25.6 g of magnesium nitrate hexahydrate in 15 mL deionized water. Tween 20 (50 mg) was added, followed by 2.64 g of (S)-(+)-abscisic acid (10 mmoles of 95% purity). Addition of the theoretical amount of concentrated aqueous ammonium diluted with 5 mL of water and stirring briefly brought all the abscisic acid into solution. The mixture was made up to 50 mL with deionized water and filtered. Analysis of the solution by HPLC showed 5.0% of (S)-(+)-abscisic acid.

An aqueous solution composition comprising 5% abscisic acid by weight as the ammonium salt and further comprising 51% by weight magnesium nitrate as a performance enhancing additive was prepared.

Example 9

The effect of ABA alone, ABA ammonium salt, ABA ammonium salt+ammonium nitrate, ABA ammonium salt+ammonium nitrate+urea, ABA ammonium salt+ammonium nitrate+calcium chloride, or ABA ammonium salt+magnesium nitrate on tomato leaf transpiration was studied (Table 4). All treatments contained 250 ppm ABA or ABA salts at a concentration equivalent to 250 ppm ABA. ABA ammonium salt showed similar transpiration inhibition to ABA over the 3-day period. ABA ammonium salt+ammonium nitrate, ABA ammonium salt+ammonium nitrate+urea, ABA ammonium salt+ammonium nitrate+calcium chloride, or ABA ammonium salt+magnesium nitrate showed more transpiration inhibition than ABA or ABA ammonium salt. Compared among tested treatments, ABA ammonium salt+ammonium nitrate+urea and ABA ammonium salt+magnesium nitrate had more transpiration inhibition than ABA ammonium salt+ammonium nitrate and ABA ammonium salt+ammonium nitrate+calcium chloride. There was no difference between ABA ammonium salt+ammonium nitrate and ABA ammonium salt+ammonium nitrate+calcium chloride. This suggested no further transpiration inhibition by adding calcium chloride to ammonium chloride. Results demonstrate that nitrogen-containing fertilizer in ABA salt formulation improves ABA salt performance for transpiration inhibition. There was difference among different nitrogen-containing fertilizers on ABA performance enhancing.

TABLE 4

Effect of different nitrogen-containing fertilizer on improving ABA ammonium salt performance for tomato leaf transpiration inhibition

| Treatment | Transpiration rate (% of control) Days after treatment | | | |
|---|---|---|---|---|
| | 1 | 2 | 3 | Average |
| Control | 100 | 100 | 100 | 100 |
| 250 ppm ABA | 59.35 | 71.02 | 77 | 69 |
| 250 ppm ABA ammonium salt | 57 | 67 | 78 | 68 |
| 250 ppm ABA ammonium salt + ammonium nitrate | 43 | 61 | 52 | 52 |
| 250 ppm ABA ammonium salt + ammonium nitrate + urea | 27 | 48 | 53 | 43 |
| 250 ppm ABA ammonium salt + ammonium nitrate + calcium chloride | 46 | 63 | 71 | 60 |
| 250 ppm ABA ammonium salt + magnesium nitrate | 34 | 43 | 47 | 41 |

Example 10

Preparation of an Aqueous Solution Composition of the Ammonium Salt of (S)-(+)-Abscisic Acid Comprising Ammonium Acetate (S)-(+)-abscisic acid (2.64 g, 10 mmoles of 95% purity) was suspended in a solution of 50 mg Tween 20 in 8 mL water and stirred while adding 10 mmoles of concentrated aqueous ammonia. All the abscisic acid dissolved to give a clear solution. Ammonium acetate (7.71 g, 100 mmol) was added and dissolved. The solution was made up to a final volume of 20 mL by addition of water.

An aqueous solution composition comprising 12.5% (S)-(+)-abscisic acid by weight as the ammonium salt and further comprising 38.5% by weight ammonium acetate as a performance enhancing additive was prepared.

Example 11

The effect of ABA ammonium salt and ABA ammonium salt+ammonium acetate on tomato leaf transpiration was studied (Table 5). Both ABA salts were at concentration equivalent to 250 ppm ABA. ABA ammonium salt+ammonium acetate decreased more transpiration at 1 and 2 days after treatment than ABA alone or ABA ammonium salt alone. Results demonstrated that ammonium acetate could also be used to increase ABA salt performance for transpiration inhibition.

TABLE 5

Effect of ABA ammonium salt with ammonium acetate on tomato leaf transpiration

| Treatment | Transpiration rate (% of control) Days after treatment | | | |
|---|---|---|---|---|
| | 1 | 2 | 3 | Average |
| Control | 100 | 100 | 100 | 100 |
| 250 ppm ABA | 71 | 75 | 88 | 78 |
| 250 ppm ABA ammonium salt | 76 | 78 | 88 | 81 |
| 250 ppm ABA ammonium salt + ammonium acetate | 60 | 59 | 85 | 68 |

Example 12

The effect of calcium chloride (1, 10, or 100 mM) alone and its combination with 250 ppm ABA was examined (Table 6). Calcium chloride alone at 1, 10, or 100 mM did not affect tomato leaf transpiration. However, plants treated with the combination of 10 or 100 mM calcium chloride with 250 ppm ABA had a significantly lower transpiration rate than plants treated with ABA alone. Results demonstrate that calcium chloride can be employed as an adjuvant to improve ABA performance.

TABLE 6

Effect of calcium chloride alone or its combination with ABA on inhibition of tomato leaf transpiration

| Treatment | Transpiration rate (% of control) |
|---|---|
| Control | 100 |
| 250 ppm ABA | 76 |
| 1 mM $CaCl_2$ | 101 |
| 10 mM $CaCl_2$ | 98 |
| 100 mM $CaCl_2$ | 97 |
| 250 ppm ABA + 1 mM $CaCl_2$ | 79 |
| 250 ppm ABA + 10 mM $CaCl_2$ | 62 |
| 250 ppm ABA + 100 mM $CaCl_2$ | 58 |

Data listed in this table are the average values over the first 3 days after treatment.

Example 13

Preparation of an Aqueous Solution Composition of the Ammonium Salt of (S)-(+)-Abscisic Acid Comprising Both Ammonium Nitrate and Calcium Chloride A solution of calcium chloride dihydrate (14.7 g, 100 mmoles) was prepared in 10 mL of water. Tween 20 (50 mg)

was added, followed by 2.64 g of (S)-(+)-abscisic acid (10 mmoles of 95% purity). Addition of the theoretical amount of concentrated aqueous ammonia produced a gummy mixture. Addition of ca. 30 mL additional deionized water and stirring overnight finally gave a clear solution. Ammonium nitrate (8.00 g, 100 mmoles) was added, and it dissolved easily. The volume of the final solution was measured to be 67 mL, corresponding to 3.7% (S)-(+)-abscisic acid by weight to volume.

An aqueous solution composition comprising 3.7% abscisic acid by weight as the ammonium salt and further comprising 11.9% by weight ammonium nitrate plus 21.9% calcium chloride dihydrate as performance enhancing additives was prepared.

Example 14

The effect of ABA alone, ABA ammonium salt, or ABA ammonium salt+ammonium nitrate+calcium chloride on tomato leaf transpiration was studied (Table 7). All treatments contained 250 ppm ABA or ABA salts at a concentration equivalent to 250 ppm ABA. ABA ammonium salt showed similar transpiration inhibition as ABA over the 3-day period. ABA ammonium salt+ammonium nitrate+calcium chloride showed more transpiration inhibition than ABA or ABA ammonium salt. Results demonstrate that adding the combination of nitrogen-containing fertilizer and calcium-containing fertilizer in ABA salt formulation improves ABA salt performance for transpiration inhibition.

TABLE 7

Effect of combination of nitrogen-containing fertilizer and calcium-containing on improving ABA ammonium salt performance for tomato leaf transpiration inhibition

| Treatment | Transpiration rate (% of control) Days after treatment | | | |
|---|---|---|---|---|
| | 1 | 2 | 3 | Average |
| Control | 100 | 100 | 100 | 100 |
| 250 ppm ABA | 59 | 71 | 77 | 69 |
| 250 ppm ABA ammonium salt | 57 | 67 | 78 | 68 |
| 250 ppm ABA ammonium salt + ammonium nitrate + calcium chloride | 46 | 63 | 71 | 60 |

Example 15

The effect of foliar application of 100 mM urea and its combination with 250 ppm ABA on tomato was studied (Table 8). At 4 days after treatment, 100 mM urea caused leaf injury. The combination of 100 mM urea with ABA significantly decreased the number of injured leaves from 11.8 injured leaves per plant without ABA to 0.5 injured leaves per plant with ABA. Results indicated that ABA could be used as a safening agent to reduce the phytotoxicity caused by high concentration of foliar fertilization of urea.

TABLE 8

Effect foliar applied urea and its combination with ABA on tomato leaf phytotoxicity at 4 days after treatment.

| Treatment | Number of injured leaf |
|---|---|
| Control | 0.0 |
| 250 ppm ABA | 0.0 |

TABLE 8-continued

Effect foliar applied urea and its combination with ABA on tomato leaf phytotoxicity at 4 days after treatment.

| Treatment | Number of injured leaf |
|---|---|
| 100 mM Urea | 11.8 |
| 250 ppm ABA + 100 mM Urea | 0.5 |

Example 16

The effect of foliar application of 100 mM ammonium nitrate or its combination with 250 ppm ABA on tomato was studied (Table 9). At 4 days of treatment, 100 mM urea caused leaf injury. The combination of 100 mM ammonium nitrate with ABA significantly decreased the number of injured leaves from 8.8 injured leaves per plant without ABA to 5.3 injured leaves per plant with ABA. Results indicated that ABA could be used as a safening agent to reduce the phytotoxicity caused by high concentration of foliar fertilization of ammonium nitrate.

TABLE 9

Effect ammonium nitrate and its combination with ABA on tomato leaf phytotoxicity at 4 days after treatment.

| Treatment | Number of Injured leaves |
|---|---|
| Control | 0.0 |
| 250 ppm ABA | 0.0 |
| 100 mM $NH_4NO_3$ | 8.8 |
| 250 ppm ABA + 100 mM $NH_4NO_3$ | 5.3 |

The invention claimed is:

1. A liquid agricultural composition comprising ABA or its salts and a nitrogen and/or 10-100 mM of calcium containing fertilizer or salt, provided that the composition does not contain thiosulphate or salicylic acid or derivatives thereof.

2. The composition of claim 1 wherein the fertilizer is urea.

3. The composition of claim 1 wherein the fertilizer is ammonium nitrate.

4. The composition of claim 1 wherein the fertilizer is calcium chloride.

5. A method for enhancing and extending the effect of ABA on plants which comprises applying an effective amount of the composition of claim 1 to a plant.

6. The method of claim 5 wherein the nitrogen-containing fertilizer is urea.

7. The method of claim 5 wherein the nitrogen-containing fertilizer is ammonium nitrate.

8. The method of claim 5 wherein the calcium-containing fertilizer is calcium chloride.

9. The method of claim 5 that further comprises adding a magnesium containing fertilizer to the composition.

10. A method for enhancing and extending inhibition of transpiration which comprises applying an effective amount of the composition of claim 1 to a plant.

11. The method of claim 10 wherein the nitrogen-containing fertilizer is urea.

12. The method of claim 10 wherein the nitrogen-containing fertilizer is ammonium nitrate.

13. The method of claim 10 wherein the calcium-containing fertilizer is calcium chloride.

14. The method of claim 10 that further comprises adding a magnesium containing fertilizer to the composition.

15. A method of reducing the phytotoxicity of foliar-applied fertilizers comprising adding an effective amount of ABA or its salts as a solution to the fertilizer before or with application of the fertilizer, where the fertilizer is a nitrogen and/or 10-100 mM of calcium containing fertilizer or salt, to a plant susceptible to phytotoxicity, provided that no thiosulphate or salicylic acid or derivatives thereof, is applied to said plant.

16. The method of claim 15 wherein the fertilizer is urea.

17. The method of claim 15 wherein the fertilizer is ammonium nitrate.

18. The method of claim 15 wherein the fertilizer is calcium chloride.

* * * * *